(12) United States Patent
Yu et al.

(10) Patent No.: US 10,704,110 B2
(45) Date of Patent: Jul. 7, 2020

(54) METHOD FOR RECOVERING SUGAR SOLUTION PREPARED BY SACCHARIFICATION OF BIOMASS

(71) Applicant: Korea Research Institute of Chemical Technology, Daejeon (KR)

(72) Inventors: Ju-Hyun Yu, Daejeon (KR); In-Yong Eom, Daejeon (KR); Kyung-Sik Hong, Sejong (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/319,167

(22) PCT Filed: Jul. 24, 2017

(86) PCT No.: PCT/KR2017/007965
§ 371 (c)(1),
(2) Date: Jan. 18, 2019

(87) PCT Pub. No.: WO2018/021782
PCT Pub. Date: Feb. 1, 2018

(65) Prior Publication Data
US 2019/0284648 A1    Sep. 19, 2019

(30) Foreign Application Priority Data

Jul. 27, 2016 (KR) .................. 10-2016-0095286
Oct. 26, 2016 (KR) .................. 10-2016-0140275

(51) Int. Cl.
| | | |
|---|---|---|
| C13K 1/04 | (2006.01) | |
| B01D 21/26 | (2006.01) | |
| B01D 25/12 | (2006.01) | |
| C12P 19/02 | (2006.01) | |
| C12P 19/14 | (2006.01) | |

(52) U.S. Cl.
CPC .............. *C13K 1/04* (2013.01); *B01D 21/262* (2013.01); *B01D 25/12* (2013.01); *C12P 19/02* (2013.01); *C12P 19/14* (2013.01)

(58) Field of Classification Search
None
See application file for complete search history.

(56) References Cited

U.S. PATENT DOCUMENTS

| | | | |
|---|---|---|---|
| 8,728,320 B2 | 5/2014 | Borden | |
| 9,328,365 B2 * | 5/2016 | Tanaka | ............ C12P 19/02 |
| 2013/0266991 A1 | 10/2013 | Kanamori et al. | |
| 2015/0344921 A1 | 3/2015 | Kacmar et al. | |

FOREIGN PATENT DOCUMENTS

| | | |
|---|---|---|
| WO | WO 2015/107415 A1 | 7/2015 |
| WO | WO-2015107415 A1 * | 7/2015 |

OTHER PUBLICATIONS

Piazza, G et al. J. Chem Technol. Biotechnol. 2015 vol. 90 pp. 1419-1425.*
Oct. 25, 2017 English translation of International Search Report for PCT/KR2017/007965.
George J. Piazza et al., "Flocculation of Kaolin and Lignin by Bovine Blood and Hemoglobin," J Chem Techno Biotechnol 2015, vol. 90, pp. 1419-1425 (Jul. 3, 2014).

* cited by examiner

*Primary Examiner* — Heidi Reese
(74) *Attorney, Agent, or Firm* — Hahn Loeser & Parks, LLP (57) ABSTRACT

The present invention relates to a method for effectively recovering a sugar solution containing glucose and saccharogenic residues after saccharification using an acid or a saccharification enzyme of a wood-based or algae biomass, and a device for implementing the method. More specifically, the present invention relates to a method capable of recovering a sugar solution using minimal equipment and water after aggregating fine particles by adding a protein suspension to a suspension of glucose and saccharogenic residues which are produced by saccharifying cellulose by adding an acid or saccharification enzyme to the biomass, while capable of minimizing an amount of saccharide lost in the residues, and a device for implementing the method.

6 Claims, 2 Drawing Sheets

METHOD FOR RECOVERING SUGAR SOLUTION PREPARED BY SACCHARIFICATION OF BIOMASS

TECHNICAL FIELD

The present disclosure relates to a method for efficiently recovering a sugar solution from saccharification products containing glucose and saccharification residues after saccharification of lignocellulosic or algal biomass using acids or saccharification enzymes and an apparatus for implementing the method, and more particularly, to a method for recovering a sugar solution prepared by saccharification of biomass, including a biomass saccharification products production step of carrying out saccharification of pretreated biomass with an addition of enzymes or acids; an aggregation step of fine particles by adding a protein additive for saccharification residues aggregation to the saccharification products of biomass and mixing to prepare a slurry in which fine particles aggregated by aggregation step of the enzymatic saccharification products; and a sugar solution recovery step of separating and recovering a sugar solution by centrifugation or filtration of the slurry containing aggregated fine particles, and an apparatus for implementing the same.

The present application is a U.S. national stage of international application no. PCT/KR2017/007965, filed on 24 Jul. 2017, which claims priority to Korean Patent Application No. 10-2016-0095286 filed on Jul. 27, 2016 in the Republic of Korea and Korean Patent Application No. 10-2016-0140275 filed on Oct. 26, 2016 in the Republic of Korea, the disclosure of which is incorporated herein by reference.

BACKGROUND ART

Lignocellulosic biomass that is a renewable resource as an alternative to fossil fuels including petroleum and coal is evaluated as a major means for transition to biobased economy through conversion to bioalcohol as transportation fuel and lignocellulosic sugar which is an industrial fermentable sugar. Some developed countries including USA have already started the industrial production of bioethanol using lignocellulosic biomass as a raw material, and a recent report says that Renmatix and Sweetwater in USA commence the industrial production of industrial fermentable sugars from lignocellulosic biomass in 2017. The lignocellulosic biomass resource used is refinery by-products of woods and corns, and cellulose, which is one of the structural components of biomass, is a direct raw material of bioalcohol or industrial fermentable sugar.

Additionally, algal biomass including green algae and diatoms gains attention as third generation biomass and has been studied and developed to achieve commercialization, and it contains not only carbohydrate such as starch and cellulose but also protein and oil in the body and is a promising raw material of biofuels including bioethanol, biodiesel and foods. In algal biomass, green algae and diatoms mainly containing starch or cellulose do not have lignin in the body unlike lignocellulosic biomass, and do not need high-temperature pretreatment that is generally applied to lignocellulosic biomass, and carbohydrate present in the body, for example, starch and cellulose, is easily converted to monosaccharides by acids or starch degrading enzymes and cellulase.

To convert cellulose in biomass to glucose, acids or saccharification enzymes are added to the pretreated product containing cellulose as one of the main components obtained by pretreatment of biomass, and saccharification is carried out at a specified temperature for a predetermined time. The resulting saccharification products contain saccharification residues, for example, lignin, remaining nonhydrolyzed in solid state in a sugar solution in which monosaccharides of glucose or wood sugar produced by hydrolysis of cellulose or hemicellulose are dissolved. It is well known that the saccharification residues containing lignin as a main component have hydrophobic surface, so that the reduction of enzyme activity is occurred by irreversible adsorption of enzyme on it during enzymatic saccharification, which causes long saccharification time and yield loss.

To solve this problem, U.S. Pat. No. 8,728,320B discloses the addition of exogenous protein to a reaction system, binding to the surface of lignin to reduce the adsorption inactivation of enzymes, and adsorption of water-soluble lignin to protein and removal. But this technology does not yet propose a technical solution for effective solid-liquid separation to prepare a high concentration sugar solution and does not consider a method for reusing a considerable amount of active enzymes left after enzymatic saccharification.

In the case of bioethanol production with biomass as a raw material, many nutrients for microorganism cultivation including a source of nitrogen, for example, ammonia, are added to the saccharification products, and after inoculation of microorganisms and cultivation for a predetermined time, monosaccharides, for example, glucose, are converted to ethanol. Subsequently, after evaporation of ethanol by heating a fermentation broth in whole or in part, ethanol can selectively be recovered by condensing ethanol vapor.

In contrast, in the case of fermentable sugar (biosugar) production for microorganism cultivation using biomass as a raw material, a sugar solution is recovered from the saccharification products, and a purification process for removing impurities other than sugar and a concentration process for preparing a higher concentration sugar solution are additionally performed. To recover a sugar solution, it is necessary to remove insoluble solid particles from the saccharification products, and it is general to carry out filtration or centrifugation. For example, US2015/0344921A1 discloses centrifugation or filtration of saccharification products as they are, to recycle enzymes after saccharification. In addition, US2015/0344921A1 also discloses recovering and reusing enzymes from the filtrate.

However, when a centrifuge, for example, a centrifugal decanter, is used to recover a sugar solution from saccharification products containing a large amount of sugars, thus having higher specific gravity than water and containing even fine particles, it is necessary to spin it (for example, 60 or more minutes at 1,776×g per min) for a long time even by high speed rotation, and thus the energy cost is never low so that it may not be practical. Even in the case of membrane filtration to prepare a clear sugar solution, filtration itself is not easy and fine particles still remain after filtration. So, additional treatment, for example, microfiltration, is inevitable because fine particles clog the separator or filter cloth holes and the pressure increases rapidly. Additionally, when performing a solid-liquid separation of a slurry containing fine particles by filtration, it is known that a mineral additive, for example, a filter aid, is generally used.

For this reason, the filtration or centrifugation is occasionally carried out after aggregation of fine particles with an addition of polymeric flocculants. In this instance, the polymeric flocculants may be synthetic ionic or non-ionic chemicals with molecular weight of a few hundred thousand or more. And, the larger the amount of particles to be aggregated, the larger the amount of polymeric flocculants that are necessary to be used. Accordingly, when saccharification products produced from lignocellulosic biomass as a raw material contain a high concentration of sugar and a few % of insoluble saccharification residues as well, an amount of polymeric flocculants needed increases greatly, and the preparation cost of the resulting sugar solution inevitably increases. Additionally, this does not rule out the possibility of contamination of the sugar solution by the remaining polymer compound and its consequential limited use.

Meanwhile, in the case of saccharification of biomass using enzymes, after enzymatic saccharification, the saccharification products may be heated to denature the enzymes that are already included in the saccharification products so that the enzymes have the ability to aggregate by themselves, and solid-liquid separation may be carried out (US2015/0354017A1). However, the saccharification enzymes (cellulase complex formulation) that are never cheap still remain in the saccharification products produced by enzymatic saccharification of pretreated lignocellulosic biomass, and it is known that a considerable amount of these enzymes still maintain enzyme activity even after saccharification (Novozymes's Product Sheet, Special Food/2001-08524-03.pdf). Like US Patent Publication No. US2015/0344921A1, the technology for separation, recovery and recycling of enzymes by ultrafiltration in the process of producing fermentable sugar using lignocellulosic biomass as a raw material is already suggested by many people. Accordingly, because thermal denaturation of saccharification enzymes by heating the enzymatic saccharification products of biomass and the use of the aggregation ability of the denatured protein for solid-liquid separation results in the giving up of an opportunity to use a considerable amount of active enzymes left even after enzymatic saccharification, it is not desirable.

Accordingly, after conducting a lot of efforts to develop a technology that prepares a high concentration sugar solution by easily performing a solid-liquid separation of saccharification products of biomass without using the aggregation ability of denatured enzymes, and recovers a sugar solution containing enzymes by this effective solid-liquid separation to reuse a considerable amount of active enzymes left even after enzymatic saccharification, the inventors finally completed the present invention.

DISCLOSURE

Technical Problem

The inventors intended to develop a method for separating a clear sugar solution that hardly contains fine particles and insoluble saccharification residues using few processes and minimum energy and use of equipment for implementing the method process from the saccharification products of biomass including a high concentration of monosaccharides and a few percentages of insoluble particles.

Additionally, the inventors intended to develop a technology that can reuse a considerable amount of active enzymes left even after enzymatic saccharification by recovering a sugar solution containing saccharification enzymes by effective solid-liquid separation.

Technical Solution

To solve the above-described problem, the present disclosure provides a method that adds a protein additive that is a water-soluble or water-dispersible protein in water to saccharification product and mix to induce aggregation of fine particles into macroparticle, and carries out centrifugation or filtration, and an apparatus for implementing the same.

More particularly, the present disclosure provides a method for efficiently recovering a sugar solution containing enzymes from saccharification products of biomass, including adding an aqueous vegetable or animal protein having hydrophobic surface on the protein by a solution or suspension to saccharification products of biomass, and mixing to induce aggregation of fine particles to be macroparticles; primary solid-liquid separation by carrying out centrifugation or filtration of a slurry containing the macroparticles at low rotation speed for a short time to recover a sugar solution; recovering the solid residues, i.e., a precipitate sunk by centrifugation or solids left on the filter cloth by filtration; and lightly mixing with deionized water to prepare a secondary slurry; and carrying out high speed centrifugation or pressure filtration of the slurry to recover the remaining sugar solution.

Additionally, the present disclosure provides an apparatus for recovering a sugar solution in which, after adding a protein aqueous solution or suspension having hydrophobic surface on the protein to saccharification products and mixing, continuous centrifugation is carried out using a centrifugal decanter, and the discharged solids are remixed with fresh water while transferring to next step to increase the volume, and then fed into a filter press, and pressure filtration is earned out.

Advantageous Effects

According to the present disclosure, a sugar solution containing enzymes is recovered from a slurry containing glucose and saccharification residues produced by saccharification of biomass by solid-liquid separation using a minimum number of equipment and a minimum amount of water, thereby maximizing the sugar recovery and remarkably reducing the number of apparatus and the operation time, resulting in the reduced equipment and management costs.

Additionally, a considerable amount of active enzymes remaining even after enzymatic saccharification can be collected to reuse, and thus a higher concentration sugar solution can be produced at low costs.

BEST MODE

Hereinafter, the present disclosure will be described in detail. It should be understood that the terms or words used in the specification and the appended claims should not be construed as limited to general and dictionary meanings, but interpreted based on the meanings and concepts corresponding to the technical aspects of the present disclosure on the basis of the principle that the inventor is allowed to define terms appropriately for the best explanation.

The phrase "saccharification products of biomass" as used herein refers to a slurry in which monosaccharides and insoluble solid particles obtained by hydrolysis of lignocellulosic biomass or algal biomass using saccharification enzymes or acids are dispersed in water. Additionally, the phrase "saccharification residues" refers to solids that are insoluble in water containing a component that cannot be hydrolyzed any more, such as lignin, as the main component after conversion of cellulose or hemicellulose to monosaccharides through hydrolysis of biomass by enzymes or acids.

In the present disclosure, a protein additive for saccharification residues aggregation (hereinafter abbreviated to a protein additive) added for promoting the solid-liquid separation of saccharification products of biomass refers to an additive whose main component is general protein except cellulase used for enzymatic saccharification of biomass. The protein additive includes, without any particular limitation, any type of additive whose main component is protein or polypeptide having hydrophobic surface on it. The most effective protein additive for solid-liquid separation of saccharification products of the present disclosure contains globular protein as the main component and preferably has aggregation or adsorption property to the hydrophobic surface induced by thermal denaturation or acidity (pH) adjustment. Its example includes additives whose main component is soy protein, egg albumin, ovalbumin, human serum albumin, bovine serum albumin and globulin. Another protein additive that can be used for solid-liquid separation of the present disclosure includes fibrous protein or scleroprotein as the main component and has hydrophobic surface within protein in part and thus has a property of aggregation. The protein additive includes additives whose main component is keratin, collagen, fibroin, elastin, and one of reserve protein, gluten.

The present disclosure provides a method for recovering a sugar solution prepared by saccharification of biomass, including biomass saccharification products production by carrying out the saccharification of pretreated biomass with acids or saccharification enzymes; fine particles aggregation by adding a protein additive for saccharification residues aggregation to the saccharification products of biomass and mixing to prepare a slurry containing aggregated particles; and sugar solution recovery by carrying out centrifugation or filtration of the slurry containing aggregated particles to obtain a sugar solution.

In the method for recovering a sugar solution prepared by saccharification of biomass according to the present disclosure, the fine particles aggregation step may include adding a protein additive for saccharification residues aggregation in the form of an aqueous solution or suspension.

In the method for recovering a sugar solution prepared by saccharification of biomass according to the present disclosure, the protein additive for saccharification residues aggregation has hydrophobic surface in the molecule structure of protein even in part, and thus may form a suspension by heating or adjusting the acidity (pH) of an aqueous solution after dissolving in water.

In the present disclosure, according to a method for preparing the protein additive added to the saccharification products of biomass for solid-liquid separation of the saccharification products, first, protein is dissolved or suspended in water. Before adding to the saccharification products, a suspension prepared by heating the protein aqueous solution or suspension at 80 to 121° C. to induce thermal denaturation is more effective. In this instance, for effective denaturation of protein, a method that adjusts the acidity (pH) of the saccharification products including the protein aqueous solution or suspension and the protein for aggregation may be used. The protein concentration in the protein aqueous solution or suspension is preferably 100 mg/L to 100 g/L, and more preferably 500 mg/L to 50 g/L. The total amount of protein added to the saccharification products preferably increases according to an amount of insoluble solids or saccharification residues in the saccharification products, and its amount may be 0.01 g to 100 g per 1 kg of the saccharification residues, and preferably 0.1 g to 10 g per 1 kg of the saccharification residues.

In the present disclosure, a method for most effective aggregation of fine particles in the saccharification products at a minimum loss of saccharification enzymes using the protein additive or the aqueous solution or suspension prepared for solid-liquid separation of the saccharification products of biomass is to slowly add the protein aqueous solution or suspension while mixing the saccharification products at a speed at which precipitation does not occur and keep mixing for a predetermined time.

In the method for recovering a sugar solution prepared by saccharification of biomass according to the present disclosure, the sugar solution recovery step may use one of a centrifuge, a filter press and a centrifugal decanter.

The present disclosure additionally provides a method for recovering a sugar solution from saccharification products of biomass at a minimum loss of sugar by a minimum number of processes. To this end, 1) adding a water-soluble or water-dispersible protein aqueous solution or suspension to saccharification products including saccharification residues and stirring to induce aggregation of fine particles in the saccharification products to be macroparticles, 2) transferring the saccharification products containing the converted macroparticles to a centrifuge or a filtration device and carrying out centrifugation at a low rotation speed for a short time or filtration without applying high pressure to recover a sugar solution, 3) recovering the saccharification residues either precipitated by centrifugation or left in the filter cloth after filtration, and mixing with an addition of water so that the volume of the slurry increases by dilution, and 4) transferring the volume increased slurry to the centrifuge or filtration device and carrying out high speed centrifugation or pressure filtration to recover the remaining sugar solution.

In the present disclosure, the saccharification products to separate solid and liquid contain a large amount of saccharification residues in a sugar solution, produced by hydrolysis of cellulose and hemicellulose using cellulases, and for example, they are the enzymatic hydrolysate of lignocellulosic biomass including agricultural by-products such as corn stover, sunflower stalks, empty fruit bunch of oil palm and palm trunk, energy crop including miscanthus and reed, and woody biomass including eucalyptus, acacia, willow, poplar hybrid, and the enzymatic hydrolysate of algal biomass including green algae such as chlorella and diatoms.

According to a method for recovering a sugar solution from the enzymatic hydrolysate of biomass of the present disclosure, a clear sugar solution and saccharification residues containing a small portion of the sugar solution are obtained by solid-liquid separation of saccharification products in which fine particles of saccharification residues containing lignin as a main component are aggregated and converted to macroparticles. According to the Stock's law, the speed at which solid particles sink in a liquid is proportional to the density difference between the solid particles and the medium, and is proportional to the square of the particle size, and thus solid-liquid separation of the saccharification products containing the converted macroparticles is finished in a short time at even low-speed centrifugation. Additionally, the particles increased in size make filtration with a filter cloth efficient for obtaining a clear sugar solution. However, because a portion of sugar solution still remains in the precipitate or filtration residues even after solid-liquid separation, a subsequent process for recovering a sugar solution is additionally necessary, but in the subsequent process, to easily disintegrate the precipitate or filtration residues when adding water and mixing, high-speed centrifugation or high-pressure filtration is not recommended. Additionally, to increase the sugar recovery, before centrifugation or filtration, a predetermined amount of water may be added, and mixing may be performed, and after that, solid-liquid separation may be carried out again.

The method for recovering a sugar solution prepared by saccharification of biomass according to the present disclosure may further include, after the first sugar solution recovery step, adding water to the saccharification residues and mixing so that the slurry volume of the saccharification residues increases by dilution; and separating the sugar solution from the saccharification residues again to recover remaining sugar solution.

The method for recovering a sugar solution prepared by saccharification of biomass according to the present disclosure may further include, after the first sugar solution recovery step, adding water to the saccharification residues and mixing so that the slurry volume of the saccharification residues increases by dilution; and separating the sugar solution from the saccharification residues again to recover remained sugar solution.

That is, in the method for recovering a sugar solution from the hydrolysate of biomass using acids or saccharification enzymes according to the present disclosure, to additionally recover a sugar solution from the saccharification residues containing a portion of sugar solution left after primary solid-liquid separation, it is necessary to mix the saccharification residues produced by solid-liquid separation with water to mix it. In this instance, the volume of water added can be regulated according to an intended recovery rate of sugar solution calculated from the ratio of remaining water in the solids after solid-liquid separation in the subsequent process, and the present disclosure is not limited to a particular method, for example, stirring and shaking etc., so long as mixing of the aggregated saccharification residues with water is not hindered. The new suspension prepared in this way is still maintained in such a large particle state that it is prone to sedimentation or filtration.

In this step, the method for recovering a sugar solution from the hydrolysate of biomass using acids or saccharification enzyme according to the present disclosure carries out centrifugation or filtration of the slurry prepared with adding fresh water in the above process again to additionally recover a sugar solution. Once the recovery operation of sugar solution is finished by this step, centrifugation or filtration may use more severe conditions to minimize-sugar solutions remaining in residues, and for example, in the case of centrifugation, the rotation speed and time can be increased, and in the case of filtration, the pressure can be increased. However, to further increase the recovery of sugar solution, this process can be repeated more. This is because macroparticles produced by the aggregation with protein have relatively good durability and the adhesive strength of the denatured protein is well preserved, re-aggregation of the particles separated during blending with water, forming macroparticles, may occur.

In the method for recovering a sugar solution prepared by saccharification of biomass according to the present disclosure, the step for increasing the volume of sugar solution by dilution may be conducted in a batch or continuously. That is, in the step 3) for efficient solid-liquid separation of saccharification products of biomass of the present disclosure, for additional recovery of a sugar solution from the saccharification residues discharged after primary solid-liquid separation, a mixer may be used to mix the saccharification residues with fresh water to prepare a slurry, and both batch and continuous mixing may be used.

In the method for recovering a sugar solution prepared by saccharification of biomass according to the present disclosure, the step for recovering the volume increased saccharification products may be conducted with one of a filter press and a centrifugal decanter. That is, the step 4) for efficient solid-liquid separation of enzymatic saccharification products of biomass of the present disclosure may be a repetition of step 2), and when the centrifugal decanter is used for solid-liquid separation, increasing the recovery of the sugar solution simply by increasing the rotation speed of the centrifugal decanter or the time may be a difference. Additionally, when the filter press is used for solid-liquid separation, reducing the volume of sugar solution left in the saccharification residues by increasing the compressive force may be a difference.

The method for recovering a sugar solution from the hydrolysate of biomass using saccharification enzymes according to the present disclosure additionally provides suitable type of equipment and optimal use method for minimizing used water while maximizing the recovery of the sugar solution containing saccharification enzymes as they are. In the step 1) for efficient solid-liquid separation of saccharification products of biomass, the batch or continuous saccharification machine having carried out saccharification may be used as a reactor for aggregation of fine particles with an addition of protein. That is, after saccharification, a pre-made protein aqueous solution or suspension may be fed into the saccharification reactor and keep mixing for a predetermined time to induce aggregation of fine particles by protein. In this case, to increase the recovery of the sugar solution in the solid-liquid separation of the next step, the saccharification reactor having sufficient volume is desirable to additionally feed water. Alternatively, after saccharification, the saccharification products may be transferred to a batch mixer that enables mixing, to induce an aggregation reaction of fine particles with an addition of protein. Also, in this case, to increase the recovery of the sugar solution in solid-liquid separation of the next step, the mixer having enough volume is desirable to additionally feed fresh water. Additionally, a continuous reactor may be used to mix while adding the protein aqueous solution or suspension to induce aggregation of fine particles during transfer of the saccharification products from the saccharification reactor to the solid-liquid separator, and also, in this case, to increase the recovery of the sugar solution in solid-liquid separation of the next step, the continuous mixer having enough volume is desirable to additionally feed fresh water.

That is, in the primary solid-liquid separation of the step 2) far efficient solid-liquid separation of saccharification products of biomass according to the present disclosure, the centrifugal decanter may be used to continuously supply the saccharification products in order to continuously discharge the clear sugar solution and the precipitate. Preferably, the centrifugal decanter is capable of high-speed rotation to shorten the driving time in order to reduce the power consumption. In this instance, the rotation speed is preferably equivalent to 250 x g ×5,000×g, and the residence time of the saccharification products is preferably 30 min or less. When considering the step 3) of the method for additionally recovering the sugar solution in the precipitate according to the present disclosure, because in the step 2), the centrifugal decanter discharges the soft precipitate at the same time with discharging the clear sugar solution, it is desirable to operate the centrifugal decanter to add fresh water and mix to easily prepare a slurry again, and to this end, more preferably, the rotation speed of the centrifugal decanter is equivalent to 500 ×g to 4,000×g, and the residence time of the saccharification products is 10 min or less. In most cases, even though solid-liquid separation is carried out by the centrifugal decanter that operates at high speed, because a considerable amount of sugar solution remains in the discharged precipitate, it is not possible to completely recover the sugar solution from the precipitate by a single operation of centrifugal decanting.

Additionally, in solid-liquid separation of this step, the filter press with the filter cloth having small pore size may be used. The filter press may allow some particles to pass through depending on the pore size of the filter cloth, and thus it is possible to freely select from 1 micron or less to a few tens of microns according to the intended turbidity of the sugar solution. In the present disclosure, the solid-liquid separation principle of enzymatic saccharification products of biomass is to increase the average particle size of saccharification residues in saccharification products by aggregation of fine particles containing hydrophobic lignin as the main component with an addition of protein having hydrophobic surface, so that the sedimentation speed of the particles at centrifugation becomes faster. Even though an increase in average particle size is more effective for increasing the sedimentation speed at centrifugation, because the produced macroparticles are not rigid, they may break again when compressed on the filter cloth, therefore, some of the regenerated fine particles may pass through the filter cloth. However, the amount of particles passing through the filter cloth is remarkably little, and thus the sugar solution obtained is relatively clear. In the subsequent process, a more clear sugar solution may be prepared by additional separation, for example, microfiltration. In the present disclosure, when the filter press is used for solid-liquid separation of saccharification products of biomass, the pore size of the mounted filter cloth can be freely adjusted, so it cannot be greatly limited, but 0.1 microns to 50 microns are desirable, and to prepare a clear sugar solution, 1 micron to 15 microns are more desirable.

In the method for recovering a sugar solution prepared by saccharification of biomass according to the present disclosure, the volume-increased sugar solution may be recycled to dilute the slurry in which fine particles are aggregated by an aggregation step of the enzymatic saccharification products.

In the method for recovering a sugar solution prepared by saccharification of biomass according to the present disclosure, the volume-increased sugar solution may be recycled to dilute the slurry in which fine particles aggregated by aggregation step of the enzymatic saccharification products.

That is, the sugar solution recovered from the volume-increased sugar solution of the step 4 may be recycled to dilute the slurry of the enzymatic saccharification products. For efficient separation of saccharification products of biomass of the present disclosure, after using a centrifugal decanter capable of obtaining a clear sugar solution in primary solid-liquid separation, even though the passing through of some insoluble particles is inevitable, it is desirable to use the filter press in secondary solid-liquid separation, and it is the most desirable to obtain a clear sugar solution with a reduced amount of used water by using the slightly turbid sugar solution having remarkably low sugar concentration obtained from secondary solid-liquid separation to dilute the saccharification products to increase the volume before primary solid-liquid separation.

Hereinafter, the present disclosure will be described in more detail in accordance with preparation examples and working examples. The following preparation examples and working examples are provided for illustration only, and the scope of the present disclosure is not limited thereto.

Preparation Example 1. Protein Additive for Saccharification Residues Aggregation Containing Soy Protein as a Main Component (Undenatured)

100 g of soy protein isolated (Soy protein isolated (MP Biomedicals, LLC, France) was put into a 10 liter steamer, and after adding 5 liters of deionized water, it was autoclaved at 105° C. for 20 minutes. The autoclaved soy protein aqueous solution was put into a plastic container (for 50 liters) and 45 liters of deionized water was further added to prepare a protein additive for saccharification residues aggregation.

Preparation Example 2. Protein Additive for Saccharification Residues Aggregation Containing Soy Protein as a Main Component (Thermally Denatured)

1 g of soy protein isolated (Soy protein isolated, MP Biomedicals, LLC, France) was put into a 1 liter culture bottle, and after adding 1 liter of water, it was dissolved by stirring. This was autoclaved and thermally denatured at 121° C. for 20 minutes to prepare a protein additive for saccharification residues aggregation.

Preparation Example 3. Protein Additive for Saccharification Residues Aggregation Containing Soybean Flour as a Main Component (Thermally Denatured)

1 g of soybean flour (Sigma S-9633, USA) was put into a 1 liter culture bottle, and after adding 1 liter of water, it was dissolved by stirring. This was sterilized and thermally denatured at 121° C. for 20 minutes and re-dispersed for 1 minute using a high speed homogenizer (handblender, Buwon Electronics, Republic of Korea) to prepare a protein additive for saccharification residues aggregation.

Preparation Example 4. Protein Additive for Saccharification Residues Aggregation Containing Bovine Serum Albumin as a Main Component (Thermally Denatured)

1 g of bovine serum albumin (Sigma A3059, USA) was put into a 1 liter culture bottle, and after adding 1 liter of water, it was dissolved by stirring. This was sterilized and thermally denatured at 121° C. for 20 minutes to prepare a protein additive for saccharification residues aggregation.

Preparation Example 5. Protein Additive for Saccharification Residues Aggregation Containing Egg Albumin as a Main Component (Thermally Denatured)

1 g of egg protein (Sigma A5503, USA) was put into a 1 liter culture bottle, and after adding 1 liter of water, it was dissolved by stirring. This was sterilized and thermally denatured at 121° C. for 20 minutes and re-dispersed for 1 minute using a high speed homogenizer (handblender, Buwon Electronics, Republic of Korea) to prepare a protein additive for saccharification residues aggregation.

Example A: Recovery of a Sugar Solution from Enzymatic Saccharification Products of Empty Fruit Bunch of Oil Palm Milled and hydrated product (moisture 65%) of empty fruit bunch of oil palm (supplied by Korindo Group in Indonesia) were fed into a continuous high pressure reactor (SuPR2G, Advancebio, USA) and hydrothermally pretreated at 191° C. for 20 minutes. Water was added to the pretreated product so that the water content was larger than 10 times of the dry weight of the original sample, they were mixed, and the mixture was fed into a filter press (Taeyoung filtration, Republic of Korea) to carry out solid-liquid separation. The obtained solids were dispersion milled by a cutting mill (Korea pulverizing machinery, Republic of Korea), and mixed with water. This was fed into a laboratory disc mill (Andritz, USA) and mechanical refining was carried out to prepare a substrate for enzymatic saccharification with the water content of 75.6%. 1,043 g of the saccharification substrate, 4,006 g of deionized water and 11 ml of saccharification enzyme Cellic CTec3 (Novozymes Korea, Seoul) were added to pre-weighed 7 liter saccharification reactor in total volume. The saccharification substrate was hydrolyzed enzymatically at 50±1° C., pH 5.45±0.05 and the stirring speed of 200 rpm for 72 hours to produce saccharification products. First, after weighing the content in the saccharification reactor, 50 ml of saccharification products was taken and undertook centrifugation, and the supernatant was analyzed for glucose concentration using high performance liquid chromatography (HPLC, Waters, USA). Additionally, the residues were washed with deionized water several times and freeze-dried, and the ratio of saccharification residue was calculated.

Each 40 ml of enzymatic saccharification products were transferred to a Erlenmeyer flask (125 ml). and after adding a stir bar, on a multi-stirrer (Corning USA) they were stirred at 300 rpm. 4 ml of the protein additives for saccharification residues aggregation of preparation example 1 to preparation example 5 were added to the flasks, stirred for 5 minutes and transferred to a Falcon tube for 50 ml. After carrying out centrifugation (Hanil Scientific, Republic of Korea) of the sample at 845×g for 5 minutes together with a control sample in which only 4 ml of water was added to saccharification products and they were mixed, the turbidity was measured using a turbidimeter (HACH 2100AN turbidimeter, USA), and measurements are shown in Table 1.

TABLE 1

|  | Main component of additive | Additive preparation method | Turbidity of centrifugation supernatant (NTU) |
|---|---|---|---|
| Comparative example 1 | Saccharification products control (no additive) | — | Over the limit of measurement |
| Example 1 | Soy protein isolated of preparation example 1 | No denaturation | 71 ± 35 |
| Example 2 | Soy protein isolated of preparation example 2 | Thermal denaturation | 30.8 ± 0.6 |
| Example 3 | Soybean flour of preparation example 3 | Thermal denaturation | 80.4 ± 7.1 |
| Example 4 | Bovine serum albumin of preparation example 4 | Thermal denaturation | 40.0 ± 0.6 |
| Example 5 | Egg albumin of preparation example 5 | Thermal denaturation | 69.1 ± 1.6 |

The saccharification products produced by enzymatic saccharification of the pretreated empty fruit bunch of oil palm of Example A had the glucose concentration of 2.6% (weight/weight) and specific gravity of 1.02, and the insoluble residual percentage contained in the saccharification products was about 2.0%. A sugar solution obtained by centrifugation of the saccharification products at 845×g for 5 minutes was very turbid like comparative example 1 of Table 1, so additional solid-liquid separation was inevitable. In contrast, the turbidity of the supernatant obtained by adding 4 ml (4 mg of protein) of protein additive for saccharification residues aggregation per 40 g of saccharification products (0.8 g of saccharification residues), mixing and centrifugation, is very low although it is slightly different depending on the type of protein in the protein additive for saccharification residues aggregation, and thus it can be seen that all produce a clear sugar solution.

Example B: Recovery of a Sugar Solution from Enzymatic Saccharification Products of Miscanthus Using Centrifugal Decanter and Filter Press Milled and hydrated product (moisture 65%) of empty fruit bunch of oil palm (supplied by Korindo Group in Indonesia) were fed into a continuous high-pressure reactor (SuPR2G, Advancebio, USA) and hydrothermally pretreated at 191° C. for 20 minutes. Water was added to the pretreated product so that the water content was larger than 10 times of the dry weight of the original sample, they were mixed, and the mixture was fed into a filter press (Taeyoung filtration, Republic of Korea) to carry out solid-liquid separation. The obtained solids were dispersion milled by a cutting mill (Korea pulverizing machinery, Republic of Korea), and mixed with water. This was fed into a laboratory disc mill (Andritz, USA) and mechanical refining was carried out to prepare a substrate for enzymatic saccharification with the water content of 80.7%. 48,210 g of the saccharification substrate was divided into 12 parts, and each was fed into 70 liter of saccharification reactor (Hanil Scientific, Republic of Korea) at the interval of one hour, and the saccharification reactor was maintained at 50±1° C., pH 5.0±0.05 and 200rpm. 65.8 ml of saccharification enzyme Cellic CTec3 (Novozymes Korea, Seoul) was added thereto every hour. The saccharification substrate and the saccharification enzyme were added for 12 hours in total and the saccharification was carried out for 72 hours from the initial feeding time of the substrate to produce saccharification products. Afterward, a small amount of saccharification products were taken and centrifuged, and the supernatant was analyzed for glucose concentration using high performance liquid chromatography (HPLC, Waters, USA). The solid residues of centrifugation were washed with water, dried and weighed, and a ratio of insoluble saccharification residues in the saccharification products was calculated. The saccharification products were weighed before transferring all to a mixer (Hanil Scientific, Republic of Korea) of 100 liter capacity, and the total amount of glucose was calculated using this amount and the glucose concentration.

While stirring the saccharification products at 60 rpm per min, 50 liters of the protein additive for saccharification residues aggregation of preparation example 2 was added and stirring was additionally performed for 5 minutes. This sample was transferred to a centrifugal decanter (Fine Inc., Republic of Korea) and centrifugation was carried out under the program to stay at 1,902×g for 5 minutes. The sugar solution discharged during this process was collected in a 200 liter tank. While the solids discharged from the centrifugal decanter were continuously fed into a small mixer, 72.8 liters of deionized water was added. The diluted saccharification products was fed into a filter press (Taeyoung filtration, Republic of Korea) with 5 micron-filter cloth, and pressure filtration was carried out by adjusting the pressure of the filter press so that the water content in the discharged saccharification residues is about 50%. The discharged sugar solution was fed into the centrifugal decanter again, centrifugation was carried out under the program to stay at 1,902×g for 5 minutes, and the discharged sugar solution was added to the sugar solution obtained by the decanter. A small amount of the sugar solution in the tank was taken, and the glucose concentration was measured and multiplied by the total amount of the sugar solution to calculate the sugar recovery. An average sugar recovery and a turbidity average of the final sugar solution obtained by repeating the above-described process are shown in Table 2.

Example C: Recovery of a Sugar Solution from Enzymatic Saccharification Products of Miscanthus Using Centrifugal Decanter Saccharification products were produced by the same method as Example B. While stirring the saccharification products at 60 rpm per min, 50 liters of the protein additive for saccharification residues aggregation of preparation example 2 was added and stirring was additionally performed for 5 minutes. This sample was transferred to a centrifugal decanter (Fine Inc., Republic of Korea) and centrifugation was carried out under the program to stay at 1,902×g for 5 minutes. A sugar solution discharged during this process was collected in a 300 liter tank. While solids discharged from the decanter were continuously fed into a small mixer, 74 liters of deionized water was added. Solid-liquid separation was carried out on the diluted saccharification products using the same decanter. This manipulation was repeated once more to recover the sugar solution. A small amount of the sugar solution in the tank was taken, and the glucose concentration was measured and multiplied by the total amount of sugar solution to calculate the sugar recovery. The average sugar recovery and the average turbidity of the final sugar solution obtained by repeatedly performing this process three times are shown in Table 2.

TABLE 2

| | Measurement results of Example 6 | | | | | | |
|---|---|---|---|---|---|---|---|
| Classification | Total amount (g) | Glucose concentration (%) | Total glucose (g) | Specific gravity | Residual percentage (%) | Sugar recovery (%) | Turbidity (NTU) |
| Saccharification products | 50,450 | 11.1 | 5,174 | 1.08 | 7.6 | — | Over the range |
| Example B Recovered sugar solution | 165,200 | 3.08 | 5,096 | 1.02 | 0.0 | 98.5 | 21.8 |
| Example C Recovered sugar solution | 222,000 | 2.29 | 5,075 | 1.02 | 0.0 | 98.1 | 20.2 |

In Table 2, because the saccharification products have high sugar concentration and high specific gravity, and contain a large amount of fine particles, despite centrifugation for 5 minutes at 1,902×g, some saccharification residues did not sink, and thus the turbidity was found so high that it is impossible to measure. In contrast, the sugar solution recovered by adding 0.026 g protein/g solid residue (2 g protein per 1 kg of saccharification products) as a protein additive example 2 for saccharification residues aggregation of the present disclosure was increased in volume to about 3 times or more, and had the reduced glucose concentration down to about ⅓, but a clear solution could be obtained, from which it can be seen that solid-liquid separation was efficiently accomplished. Additionally, the sugar recovery obtained from the example was found to 98.5%, and it can be seen that the sugar solution recovery technology of the present disclosure provides a very high sugar recovery by the simple process.

The sugar solution prepared using the centrifugal decanter of example C had the final volume that was four times larger than the original sugar solution, but it had a very high sugar recovery of 98% and it was clear, and thus it was desirable for sugar recovery technology.

Figure 1:
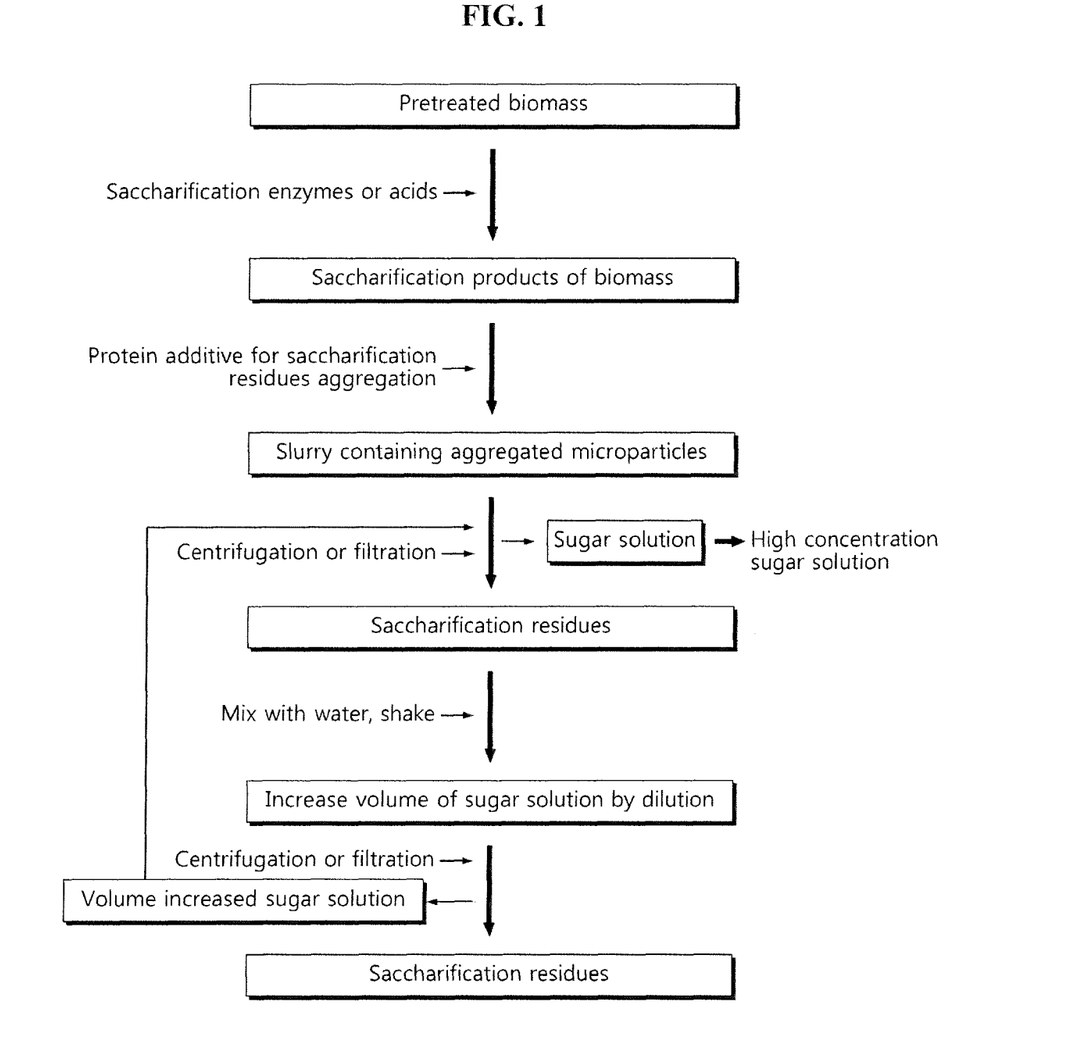
FIG. 1 is a flowchart and a conceptual diagram of processes of a method for efficiently recovering a sugar solution from saccharification products of biomass according to an implementation embodiment of the present disclosure.
Figure 2:
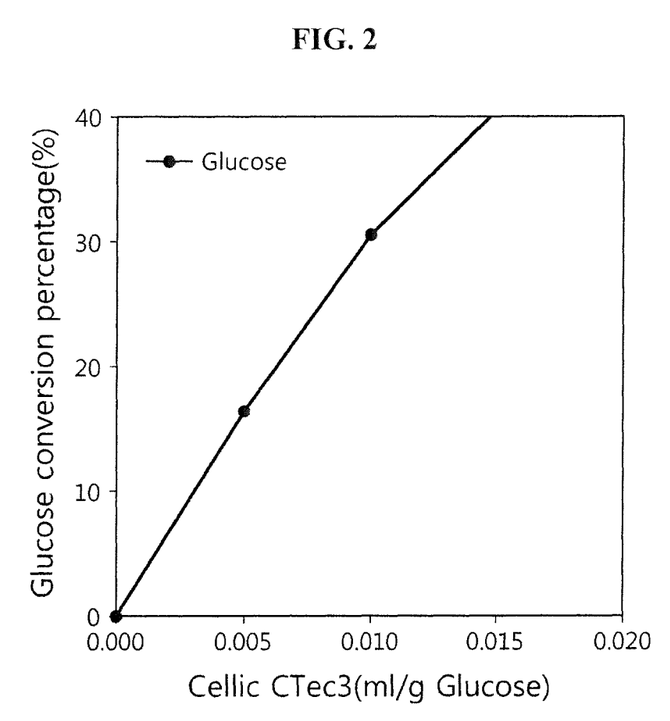
FIG. 2 is a standard curve showing the saccharification rate vs the enzyme activity in a sugar solution of saccharification products of biomass according to an implementation embodiment of the present disclosure.

Experimental Example 1: Determination of an Amount of Enzymes Contained in a Sugar Solution Recovered from Enzymatic Saccharification Products of Miscanthus Milled and hydrated product (moisture 65%) of empty fruit bunch of oil palm (supplied by Korindo Group in Indonesia) were fed into a continuous high pressure reactor (SuPR2G, Advancebio, USA) and hydrothermally pre-treated at 200° C. for 10 minutes. Water was added to the pretreated products so that the water content was larger than 10 times of the dry weight of the original sample and they were mixed, and the mixture was fed into a filter press (Taeyoung filtration, Republic of Korea) to carry out the solid-liquid separation, and fed into a cutting mill and milled to prepare a substrate for saccharification. 4061 g of deionized water was put into a saccharification reactor of 7 liter in total volume (Hanil Scientific, Republic of Korea) firstly, and 1190 g of the saccharification substrate was added. The saccharification reactor was maintained at 50±1° C., pH 5.5±0.05, and 200 rpm. 24 ml of Cellic CTec3 (Novozymes Korea, Seoul) as a saccharification enzyme was added thereto. Saccharification was carried out for 144 hours to produce saccharification products. While mixing the saccharification products by stirring, 200 g of sample was individually taken and each was put into four centrifugation tubes (500 ml) and two culture bottles. While stirring the saccharification products contained in the two centrifugation tubes using a magnetic stirrer, 200 ml of the soy protein isolated suspension of preparation example 2 was added and continued to stir for 5 minutes. Subsequently, centrifugation was carried out at 1,902×g for 5 minutes to obtain a clear supernatant. 200 ml of deionized water was added to the saccharification products contained in the two centrifugation tubes and they were mixed, and centrifugation was carried out at 1,902×g for 90 minutes to obtain a clear supernatant. 200 ml of deionized water was added to the saccharification products contained in the two culture bottles and they were put into a high temperature sterilizer (autoclave) and denatured at 121° C. for 20 minutes. The content was transferred to a centrifugation tube, and centrifugation was carried out at 1,902×g for 5 minutes to obtain a clear supernatant. 3.17 g of the substrate for saccharification was weighed and put into an Erlenmeyer flask for 125 ml, 8 ml of citrate buffer (1 M, pH 5.5, Sigma-Aldrich, USA), 1.3 ml of sodium azide (1%, w/w, Sigma-Aldrich, USA) and 24 ml of each sugar solution were added and the acidity was adjusted to pH 5.5. Deionized water was added so that the weight of the flask content was 40 g and the flask was sealed. For enzyme standard test, the saccharification system including the substrate for saccharification, the citrate buffer, sodium azide and deionized water was diluted with saccharification enzyme Cellic CTec3 and added for each capacity so that each amount is 0.01, 0.02, 0.03, 0.04 and 0.05 ml with an undiluted enzyme. The sample was put into an orbit shaker (Gaon Science, Republic of Korea) and saccharification was carried out at 50±1° C. and 200 rpm for 72 hours. After saccharification, 1 ml of saccharification products were taken, and centrifugation (11,000 rpm, 20 minutes) was carried out, and the glucose concentration in the supernatant was analyzed by high performance liquid chromatography (HPLC, Waters, USA). The results showing the saccharification rate vs the enzyme activity in the sample sugar solution using the standard curve 2 plotting the saccharification rate of the enzyme standard test are summarized in Table 3.

TABLE 3

| Classification | Saccharification rate measurement results (%) |
|---|---|
| Centrifugation after heat treatment of saccharification products | 0 |
| Centrifugation of untreated saccharification products | 11.4 ± 1.1 |
| Centrifugation after aggregation with protein additive | 15.9 ± 0.1 |

When measuring the enzyme activity in the sugar solution after different treatments of the saccharification products, it can be seen that the high-speed centrifugation supernatant contains enzymes equivalent to conversion of 11.4% of the saccharification substrate to glucose under the given condition as shown in Table 3. In contrast, when the enzymes contained in the saccharification products were denatured to induce aggregation of fine particles, the enzyme activity in the sugar solution on the newly added saccharification substrate is not observed. In contrast, the sugar solution obtained using the method of the present disclosure showed a higher enzymatic saccharification rate than the untreated sugar solution, showing that the enzyme in the sugar solution is not inactivated or removed.

What is claimed is:

1. A method for recovering a sugar solution prepared by saccharification of biomass, comprising:
    a biomass saccharification products production step of carrying out saccharification of pretreated biomass with an addition of acids or saccharification enzymes;
    an aggregation of fine particles step of adding a protein additive for aggregation of saccharification residues to the saccharification products of biomass and mixing to prepare a slurry containing aggregated fine particles; and
    a sugar solution recovery step of separating a sugar solution by centrifugation or filtration of the slurry containing aggregated fine particles;
    wherein the protein additive for aggregation of saccharification residues in a form of a suspension includes at least one additive selected from a group consisting of soy protein isolated, soy protein concentrate, and soy flour.

2. The method for recovering a sugar solution prepared by saccharification of biomass according to claim 1, wherein the sugar solution recovery step uses one of a centrifuge, a filter press and a centrifugal decanter.

3. The method for recovering a sugar solution prepared by saccharification of biomass according to claim 1, further comprising:
    after the sugar solution recovery step, mixing the saccharification residues with water to increase by dilution a volume of a remainder portion of the sugar solution that did not separate during the sugar solution recovery step but remained in the saccharification residues; and
    separating the volume-increased remainder portion of the sugar solution from the saccharification residues to recover the volume-increased remainder portion of the sugar solution.

4. The method for recovering a sugar solution prepared by saccharification of biomass according to claim 3, wherein the step of increasing the volume of the remainder portion of the sugar solution by dilution uses a batch or continuous dispersion mixer.

5. The method for recovering a sugar solution prepared by saccharification of biomass according to claim 3, wherein the step of recovering the volume-increased remainder portion of the sugar solution uses one of a filter press and a centrifugal decanter.

6. The method for recovering a sugar solution prepared by saccharification of biomass according to claim 3, wherein the volume-increased remainder portion of the sugar solution is recycled to dilute a slurry containing aggregated fine particles in continued performance of the method for recovering a sugar solution prepared by saccharification of biomass.

* * * * *

UNITED STATES PATENT AND TRADEMARK OFFICE
CERTIFICATE OF CORRECTION

PATENT NO. : 10,704,110 B2
APPLICATION NO. : 16/319167
DATED : July 7, 2020
INVENTOR(S) : Ju-Hyun Yu, In-Yong Eom and Kyung-Sik Hong Page 1 of 1

It is certified that error appears in the above-identified patent and that said Letters Patent is hereby corrected as shown below:

In the Specification

In Column 3, Line 54, delete "method".

In Column 4, Line 31, delete "earned" and substitute therefor --carried--.

In Column 9, Line 7, delete "×5,000×g" and substitute therefor --to 5,000 × g--.

In Column 9, Line 65, to Column 10, Line 2, delete the following paragraph "In the method for recovering a sugar solution prepared by saccharification of biomass according to the present disclosure, the volume-increased sugar solution may be recycled to dilute the slurry in which fine particles aggregated by aggregation step of the enzymatic saccharification products.".

Signed and Sealed this
Twenty-fifth Day of August, 2020

Andrei Iancu
*Director of the United States Patent and Trademark Office*